United States Patent [19]
Turner

[11] 3,932,493
[45] Jan. 13, 1976

[54] 3,3-(ALKYLIMINO)BIS(2-METHYLENEPROPIOPHENONE)MICROBIOCIDES

[75] Inventor: William W. Turner, Indianapolis, Ind.

[73] Assignee: Eli Lilly and Company, Indianapolis, Ind.

[22] Filed: Jan. 9, 1975

[21] Appl. No.: 539,670

[52] U.S. Cl. .................... 260/501.18; 260/501.19; 260/570.5C; 260/592; 424/316; 424/330
[51] Int. Cl.² ........................................ C07C 97/10
[58] Field of Search.... 260/501.18, 501.19, 570.5 C

[56] References Cited
OTHER PUBLICATIONS

Piskov, Zh. Obshch. Khim, Vol. 35, No. 2, pp, 228–229, (1965).

Primary Examiner—Robert V. Hines
Attorney, Agent, or Firm—Joseph A. Jones; Everet F. Smith

[57] ABSTRACT

A class of novel 3,3″-(alkylimino)bis(2-methylenepropiophenone)s has been discovered. The new compounds are readily synthesized, and are useful for the control of microorganisms, particularly soil-borne plant pathogens.

7 Claims, No Drawings

3,3-(ALKYLIMINO)BIS(2-METHYLENEPROPIO-PHENONE)MICROBIOCIDES

BACKGROUND OF THE INVENTION

This invention concerns new organic compounds, 3,3″-(alkylimino)bis(2-methylenepropiophenone)s, which are useful for the control of microorganisms, and especially of pathogens causing diseases of plants, such as fusarium root rot, which are communicated through the soil.

Such compounds have not previously been revealed. A 3-amino-2-methylenepropiophenone was prepared and described by Piskov, Zh. Obshch. Khim. 35 (2), 228–229 (1965), C.A. 62, 13079(c) (1965). No biological activities of the compound were disclosed by the Russian author.

SUMMARY

A class of new microbiocidal compounds of the following formula has been discovered and is here disclosed.

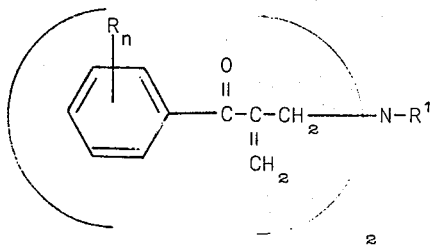

wherein:
$n$ represents 0 to 3;
R represents
$C_1$–$C_3$ alkyl,
$C_1$–$C_3$ alkoxy,
fluoro, or
phenyl;
provided that when R represents phenyl, $n$ represents 1; $R^1$ represents $C_1$–$C_2$ alkyl; and the nonphytotoxic acid addition salts thereof.

DESCRIPTION OF THE PREFERRED EMBODIMENT

In the above formula, the general terms $C_1$–$C_2$ alkyl, $C_1$–$C_3$ alkyl, and $C_1$–$C_3$ alkoxy refer to groups such as methyl, ethyl, propyl, isopropyl, methoxy and propoxy.

Suitable nonphytotoxic acid addition salts may be made by forming salts of the free bases of the above compounds with acids such as maleic, formic, hydrochloric, sulfuric, phosphoric, sulfonic, toluenesulfonic, sulfurous, benzoic, phosphonic, acetic, propionic, tartaric, methylsulfonic and hyposulfurous acids.

A group of compounds of the invention will be named below to assure that the invention is readily understood. The compounds named are, of course, merely exemplary and are not intended to delineate the scope of the invention.

3,3″-(methylimino)bis(2-methylenepropiophenone)
3,3″-(ethylimino)bis(2-methylenepropiophenone)
3,3″-(ethylimino)bis(3′-methyl-2-methylenepropiophenone), hydrochloride
3,3″-(methylimino)bis(3′,5′-diethyl-2-methylenepropiophenone), formic acid salt
3,3″-(ethylimino)bis(2-methylene-2′,4′,6′-tripropylpropiophenone), phosphonic acid salt
3,3″-(ethylimino)bis(2′-isopropyl-2-methylenepropiophenone), toluenesulfonic acid salt
3,3″-(ethylimino)bis(2′,6′-diethoxy-2-methylenepropiophenone), benzoic acid salt
3,3″-(methylimino)bis(2-methylene-4′-propoxypropiophenone), acetic acid salt
3,3″-(ethylimino)bis(2′,3′,5′-trimethoxy-2-methylenepropiophenone)
3,3″-(ethylimino)bis(2-methylene-3′-phenylpropiophenone), propionic acid salt
3,3″-(ethylimino)bis(3′,5′-difluoro-2-methylenepropiophenone), butyric acid salt
3,3″-(ethylimino)bis(3′,4′,5′-trifluoro-2-methylenepropiophenone), phosphoric acid salt
3,3″-(methylimino)bis(3′,5′-diisopropoxy-2-methylenepropiophenone)

The preferred compounds of this invention are the following.
3,3″-(methylimino)bis(2-methylenepropiophenone), maleic acid salt
3,3″-(methylimino)bis(2′,4′-dimethyl-2-methylenepropiophenone), hydrochloride
3,3″-(methylimino)bis(2′,4′-dimethyl-2-methylenepropiophenone)
3,3″-(methylimino)bis(2′,4′-dimethyl-2-methylenepropiophenone), maleic acid salt
3,3″-(methylimino)bis(2′,4′-dimethyl-2-methylenepropiophenone), phosphoric acid salt
3,3″-(methylimino)bis(2′-methyl-2-methylenepropiophenone)

The compounds of this invention are readily prepared from suitably ring-substituted 1,3-dihalo-2-benzoylpropanes. The preparation is performed in two steps which can be performed in one vessel without isolation of the intermediate product. In the first step, the stating compound is dehydrohalogenated in the presence of an inorganic base to form the intermediate product, an appropriately ring-substituted 2-(halomethyl)-acrylophenone. Reaction of the intermediate product with methylamine or ethylamine readily forms the desired product.

Both steps of the reaction may be performed at room temperature. If desired, temperatures from 0°C. to the reflux temperature of the reaction medium may be used, but in general offer no advantage over room temperature reactions. The inorganic base used in the dehydrohalogenation step of the synthesis may be any which serves to accept hydrohalide removed from the starting compound, such as alkali metal hydroxides, carbonates and bicarbonates. The preferred base is $NaHCO_3$. Since inorganic bases give off a mole of water for each mole of hydrohalide accepted, it is necessary to use a dehydrating agent, such as molecular sieves, in the reaction medium.

The reaction may be performed in any solvent which is inert to the dehydrohalogenation reaction. The preferred solvent is dimethylformamide. Other excellent reaction solvents include tetrahydrofuran and diethyl ether. In general, ethers, alkanes and aromatic solvents may be used as reaction solvents in the process.

When an acid addition salt of a compound of this invention is desired, it may be prepared by the common methods such as the simple contacting of the free base with an appropriate acid in an inert solvent such as ethyl ether or ethyl acetate.

The starting 1,3-dihalo-2-benzoylpropanes are readily prepared, as taught by Terada et al., Nippon Kagaku Zasshi 81, 612–18 (1960), C.A. 56, 1446h (1962), by the reaction of an appropriately ring-substituted acetophenone with paraformaldehyde to form the corresponding 1,3-dimethoxy-2-benzoylpropane. The dimethoxy compound is reacted at ice bath temperature with gaseous HCl to form the desired dichloro intermediate in very high yield.

The following synthetic examples are presented to assure that organic chemists can obtain the compounds of this invention without undue experimentation.

EXAMPLE 1

3,3''-(methylimino)bis(2',4'-dimethyl-2-methylenepropiophenone), hydrochloride

A mixture of 24.5 g. of 1,3-dichloro-2-(2',4'-dimethylbenzoyl)propane, 42 g. of $NaHCO_3$, 600 ml. of dimethylformamide and about 50 g. of 3A molecular sieves was stirred overnight at room temperature. In the morning, 3.87 g. of a 40 percent solution of methylamine in water was added, and the mixture was stirred for three hours more. The mixture was then filtered to remove the solids, and the filtrate was poured into water. The aqueous mixture was then extracted with ethyl ether, and the ether extract was extracted with dilute HCl. The HCl extract was made basic with dilute NaOH, and was extracted with ethyl ether. The final ether extract was then dried over $MgSO_4$, and dry HCl was bubbled through it. The product which precipitated was recrystallized from ethyl acetate/ethanol, producing 7.995 g. of 3,3''-(methylimino)bis(2',4'-dimethyl-2-methylenepropiophenone), hydrochloride, m.p. 125°–126°C. The product was identified by nuclear magnetic resonance analysis and by elemental microanalysis, the results of which follow.

|   | Theoretical | Found |
|---|---|---|
| C | 72.89% | 72.61% |
| H | 7.34 | 7.12 |
| N | 3.40 | 3.41 |

EXAMPLE 2

3,3''-(methylimino)bis(4'-methyl-2-methylenepropiophenone), maleic acid salt

A reaction mixture of 23.1 g. of 1,3-dichloro-2-(p-toluoyl)propane, 42 g. of $NaHCO_3$, and about 50 g. of 3A molecular sieves in about 600 ml. of dimethylformamide was stirred overnight at room temperature. In the morning, 3.87 g. of 40 percent methylamine solution was added, and the mixture was stirred for one hour more. The solids were filtered off, and the filtrate was poured into water which was then extracted with ethyl ether. The ether extract was extracted with dilute HCl. The HCl extract was made basic with dilute NaOH, and was extracted with ethyl ether. The final ether extract was dried over $MgSO_4$ and evaporated under vacuum to yield 8 g. of oil, which was identified by nuclear magnetic resonance analysis as 3,3'-(methylimino)bis(4'-methyl-2-methylenepropiophenone).

The maleic acid salt was made by dissolving the above product in ethyl acetate and adding an appropriate amount of maleic acid in ethyl acetate solution. The salt was purified by recrystallization from ethyl acetate/ethyl ether. The yield was 7.43 g. of pure product having a melting point of 97°–98°C. It was identified by nuclear magnetic resonance analysis and by elemental microanalysis.

|   | Theoretical | Found |
|---|---|---|
| C | 69.96% | 69.72% |
| H | 6.31 | 6.41 |
| N | 3.02 | 2.93 |

The simple synthetic process illustrated by the above examples is used, with minor variations easily supplied by an organic chemist, to make other compounds of the invention, such as the following.

EXAMPLE 3

3,3''-(methylimino)bis(2-methylenepropiophenone), maleic acid salt, m.p. 113°–115°C.

EXAMPLE 4

3,3''-(ethylimino)bis(2-methylenepropiophenone), m.p. 156°–158°C.

EXAMPLE 5

3,3''-(methylimino)bis(2'-methyl-2-methylenepropiophenone), m.p. 100°–101°C.

EXAMPLE 6

3,3''-(methylimino)bis(2'-methoxy-2-methylenepropiophenone), m.p. 124°–126°C.

EXAMPLE 7

3,3''-(methylimino)bis(2-methylene-4'-phenylpropiophenone), m.p. 175°–178°C.

EXAMPLE 8

3,3''-(methylimino)bis(4'-fluoro-2-methylenepropiophenone), oil

EXAMPLE 9

3,3''-(methylimino)bis(2',4'-dimethyl-2-methylenepropiophenone), oil

EXAMPLE 10

3,3''-(methylimino)bis(2',4',6'-trimethyl-2-methylenepropiophenone), oil

EXAMPLE 11

3,3''-(methylimino)bis(2-methylenepropiophenone), hydrochloride, oil

EXAMPLE 12

3,3''-(methylimino)bis(2-methylenepropiophenone), sulfuric acid salt, oil

EXAMPLE 13

3,3''-(methylimino)bis(2-methylenepropiophenone), formic acid salt, oil

EXAMPLE 14

3,3''-(methylimino)bis(2',4'-dimethyl-2-methylenepropiophenone), sulfuric acid salt, oil

EXAMPLE 15

3,3''-(methylimino)bis(2',4'-dimethyl-2-methylenepropiophenone), formic acid salt, oil

EXAMPLE 16

3,3''-(methylimino)bis(2',4'-dimethyl-2-methylenepropiophenone), maleic acid salt, oil

EXAMPLE 17

3,3''-(methylimino)bis(2',4'-dimethyl-2-methylenepropiophenone), phosphoric acid salt, oil

EXAMPLE 18

3,3''-(methylimino)bis(2-methylenepropiophenone), oil

EXAMPLE 19

3,3''-(methylimino)bis(3'-methyl-2-methylenepropiophenone), m.p. 115°–118°C.

EXAMPLE 20

3,3''-(methylimino)bis(4'-methoxy-2-methylenepropiophenone), m.p. 89°–92°C.

EXAMPLE 21

3,3''-(methylimino)bis(3',4'-dimethyl-2-methylenepropiophenone), m.p. 97°–99°C.

EXAMPLE 22

3,3''-(methylimino)bis(2',4',6'-trimethyl-2-methylenepropiophenone), hydrochloride, m.p. 183°–185°C.

Many compounds of this invention have been evaluated in the following test systems to determine their ability to control phytopathogenic soil-borne organisms.

TEST 1 pythium damping-off test

An aqueous dispersion of each compound to be tested was prepared by first dissolving 114 mg. of the compound in 2 ml. of acetone/ethanol, and then dispersing the solution in about 30 ml. of water containing 0.1 percent of a nonionic surfactant.

Soil was infected with *Pythium aphanidermatum*, the causative organism of pythium damping-off disease, by growing four separate isolates of the organism in cornmeal and adding portions of all four cultures to greenhouse soil which had previously been sterilized to kill wild organisms.

Four ml. of the test compound dispersion was added to 150 g. of infected soil by absorbing the dispersion on granular clay particles and mixing the particles through the soil. The treatment rate was equivalent to 44.8 kg./ha. The soil was then transferred to a small plastic pot which was planted with 12 cotton seeds. The pots were watered and placed ind a moist growth chamber until the cotton seedlings emerged, when the pots were transferred to the greenhouse for observation.

The cotton plants growing in treated soil were observed and compared with untreated control plants growing in infected soil without test compounds. The emergence and health of the treated plants were rated on a 1–5 scale, where 1 represents severe disease and 5 represents complete disease control. Results of testing typical compounds were as follows.

| Compound of Example No. | Disease Rating |
| --- | --- |
| 1 | 5 |
| 2 | 5 |
| 3 | 5 |
| 4 | 1 |
| 5 | 5 |
| 6 | 4 |

-continued

| Compound of Example No. | Disease Rating | |
| --- | --- | --- |
| 7 | 1 | |
| 8 | 5 | |
| 9 | 5 | |
| 10 | 3 | (22.4 kg./ha.) |
| 11 | 4 | |
| 12 | 1 | |
| 13 | 4 | |
| 14 | 5 | |
| 15 | 1 | |
| 16 | 5 | |
| 17 | 5 | |
| 18 | 1 | |
| 19 | 4 | (22.4 kg./ha.) |
| 20 | 3 | |
| 21 | 1 | |
| 22 | 3 | |

The compounds were sometimes tested by dusting the powdered compound on cotton seeds and planting the treated seed in infected soil. When the compounds of Examples 12, 15 and 21 were applied to seed at the rate of 4.4 g./kg. of seed in typical tests, the cotton plants showed disease rated at 4, 2, and 2 respectively.

TEST 2 fusarium root rot test

The compounds were tested in a procedure essentially similar to the procedure of Test 1, except that the infecting organism was *Fusarium solani f. phaseoli*, the causative organism of fusarium root rot, which was grown in sand mixed with fusarium-infected wheat seed. The host plant was bean, of which three seeds were planted in each pot.

Typical results were as follows:

| Compound of Example No. | Disease Rating |
| --- | --- |
| 1 | 4 |
| 2 | 4 |
| 3 | 5 |
| 4 | 4 |
| 5 | 3 |
| 6 | 1 |
| 7 | 1 |
| 8 | 1 |
| 9 | 1 |
| 10 | 1 |
| 11 | 1 |
| 12 | 1 |
| 13 | 3 |
| 14 | 1 |
| 15 | 1 |
| 16 | 3 |
| 17 | 4 |
| 18 | 4 |
| 19 | 4 |
| 20 | 4 |
| 21 | 1 |
| 22 | 4 |

The above test was varied at times by introducing the test compound as a coating of the finely powdered compound on the seed. For example, when the compound of Example 8 was applied to the bean seeds in this fashion at the rate of 4.4 g. per kg. of seed, a disease rating of 4 was obtained, indicating excellent control of the disease. In a similar test, the compound of Example 7 produced a disease rating of 3.

While the ability of the compounds to control soil-borne phytopathogens is their most important utility, the compounds also control many other microorganisms. For example, the compounds of Examples 2, 5, 6, 7, 19, 20, 21 and 22 inhibit the growth of *Staphylococ-* cus aureus; the compounds of Examples 5 and 22 control Streptococcus faecalis; the compounds of Examples 2, 5, and 20 control Erwinia amylovora; and the compounds of Examples 2, 5, 6, 7, 20 and 22 inhibit the growth of Ceratocystis ulmi.

The compounds of this invention are used for the control of soil-borne pathogens in the usual methods which agricultural chemistry has evolved for such purposes. The compounds may be applied directly to the soil in the form of a typical agricultural chemical formulation, or may be applied to the seed to be planted.

When the compounds are to be applied directly to the soil, they are most often formulated as concentrated compositions applied in the form of water dispersions or emulsions. Such water-dispersible or emulsifiable formulations are either solids usually known as wettable powders, or liquids usually known as emulsifiable concentrates. Wettable powders comprise an intimate mixture of the active compound, an inert carrier and surfactants. The concentration of the active compound is usually from about 10 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types of surfactants used for wettable powders.

The compounds are also conveniently applied to the soil in the form of solid, granular formulations. Such formulations typically comprise the compound dispersed on a granular inert carrier such as coarsely ground clay. The particle size of such granules usually ranges from about 0.1 to about 3 mm. The usual formulation process comprises dissolving the compound in an inexpensive solvent, such as kerosene or heavy aromatic naphtha, and applying the solution to the carrier in an appropriate solids mixer.

The compounds control soil pathogens when applied directly to the soil at application rates from about 5 to about 50 kg./ha. When the compounds are used by applying them to crop seed, from about 0.25 to about 5 g. of the compound should be applied to each kilogram of seed.

The compounds are applied to seed by the usual coating techniques. For example, the compounds can be finely ground and dusted onto the seed. The seed can be coated with a small amount of an oil to increase the adhesion of the compound thereon. It is also possible to dissolve the compound in a nonphytotoxic solvent, coat the seed with the solution and evaporate the solvent.

I claim:
1. A compound of the formula

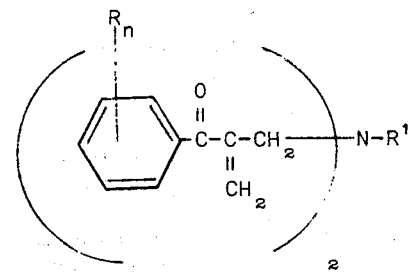

wherein:
n represents 0 to 3;
R represents
  $C_1$–$C_3$ alkyl,
  $C_1$–$C_3$ alkoxy,
  fluoro, or
  phenyl;
provided that when R represents phenyl, n represents 1; $R^1$ represents $C_1$–$C_2$ alkyl; and the nonphytotoxic acid addition salts thereof.

2. The compound of claim 1 which is 3,3''-(methylimino)bis(2-methylenepropiophenone), maleic acid salt.

3. The compound of claim 1 which is 3,3''-(methylimino)-bis(2',4'-dimethyl-2-methylenepropiophenone), hydrochloride.

4. The compound of claim 1 which is 3,3''-(methylimino)bis(2',4'-dimethyl-2-methylenepropiophenone).

5. The compound of claim 1 which is 3,3''-(methylimino)bis(2',4'-dimethyl-2-methylenepropiophenone), maleic acid salt.

6. The compound of claim 1 which is 3,3''-(methylimino)-bis(2',4'-dimethyl-2-methylenepropiophenone), phosphoric acid salt.

7. The compound of claim 1 which is 3,3''-(methylimino)bis(2'-methyl-2-methylenepropiophenone).

* * * * *

UNITED STATES PATENT AND TRADEMARK OFFICE
CERTIFICATE OF CORRECTION

PATENT NO. : 3,932,493
DATED : January 13, 1976
INVENTOR(S) : William W. Turner

It is certified that error appears in the above-identified patent and that said Letters Patent are hereby corrected as shown below:

Title of patent should read ---3,3"-(ALKYLIMINO)BIS(2-METHYLENEPROPIOPHENONE) MICROBIOCIDES---.

Column 1, line 1, "3,3-(ALKYLIMINO)" should read ---3,3"-(ALKYLIMINO)---.

Column 2, line 36, "stating" should read ---starting---.

Column 3, line 59, "3,3'-(me-" should read ---3,3"-(me- ---.

Column 5, line 51, "ind" should read ---in---.

Column 8, line 44, "thylimino)-bis" should read ---thylimino)bis---.

Column 8, line 53, "thylimino)-bis" should read ---thylimino)bis---.

Signed and Sealed this twenty-seventh Day of April 1976

[SEAL]

Attest:

RUTH C. MASON
*Attesting Officer*

C. MARSHALL DANN
*Commissioner of Patents and Trademarks*